(12) United States Patent
Tanzer et al.

(10) Patent No.: US 6,730,069 B2
(45) Date of Patent: May 4, 2004

(54) CLOTH-LIKE MECHANICAL FASTENER

(75) Inventors: Richard Warren Tanzer, Neenah, WI (US); Karen Marie Menard, Neenah, WI (US); Julius Charles Nagy, Racine, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/899,317

(22) Filed: Jul. 5, 2001

(65) Prior Publication Data

US 2003/0009144 A1 Jan. 9, 2003

(51) Int. Cl.$^7$ ................................................ A61F 13/15
(52) U.S. Cl. .................. 604/391; 604/385.23; 604/390; 24/442
(58) Field of Search .................................. 604/391, 390, 604/385.01, 385.03, 386, 387, 389; 24/442; 264/479, 167, 210.01, 210.02

(56) References Cited

U.S. PATENT DOCUMENTS

| | | |
|---|---|---|
| 3,020,613 A | 2/1962 | Morin |
| 3,387,345 A | 6/1968 | Savoir |
| 3,655,855 A | 4/1972 | Brumlik |
| 4,643,932 A | 2/1987 | Daniels |
| 4,646,397 A | 3/1987 | Yoshida |
| 4,663,220 A | 5/1987 | Wisneski et al. |
| 4,672,722 A | 6/1987 | Malamed |
| 4,704,116 A | 11/1987 | Enloe |
| 4,707,893 A | 11/1987 | Hashizume et al. |
| 4,776,068 A | 10/1988 | Smirlock et al. |
| 4,798,603 A | 1/1989 | Meyer et al. |
| 4,850,991 A * | 7/1989 | Nakanishi et al. .......... 604/387 |
| 4,870,725 A | 10/1989 | Dubowik |
| 4,881,997 A | 11/1989 | Hatch |
| 4,884,323 A | 12/1989 | Provost et al. |
| 4,920,617 A | 5/1990 | Higashinaka |
| 4,931,344 A | 6/1990 | Ogawa et al. |
| 4,937,887 A | 7/1990 | Schreiner |
| 5,081,748 A | 1/1992 | Eberle |
| 5,176,668 A | 1/1993 | Bernardin |
| 5,176,672 A | 1/1993 | Bruemmer et al. |

(List continued on next page.)

FOREIGN PATENT DOCUMENTS

| | | |
|---|---|---|
| EP | 0 217 032 B1 | 7/1986 |
| JP | 2000-210332 A | 8/2000 |
| WO | WO 95/29657 A1 | 11/1995 |
| WO | WO 97/02797 A1 | 1/1997 |
| WO | WO 97/25892 A1 | 7/1997 |
| WO | WO 97/25953 A1 | 7/1997 |
| WO | WO 97/25954 A1 | 7/1997 |
| WO | WO 99/13745 A1 | 3/1999 |

*Primary Examiner*—Weilun Lo
*Assistant Examiner*—Jacqueline F. Stephens
(74) *Attorney, Agent, or Firm*—Alyssa A. Dudkowski

(57) ABSTRACT

A cloth-like, flexible mechanical fastener including a flexible layer and at least one fastener island, and methods of making the same. The fastener island has a planar perimeter edge, a mechanical fastening material, and a backing material attached to the mechanical fastening material. The backing material is embedded within the flexible layer and the planar perimeter edge is surrounded by the flexible layer. Accordingly, the mechanical fastener offers an improved flexibility and a cloth-like presentation. The improved flexibility and cloth-like presentation reduce the potential for the wearer to be exposed to coarse edges or creases, thereby lowering the possibility of red-marking or irritation of the skin. Moreover, the flexibility of the fastener allows the fastener to better accommodate the movement of the wearer, providing more reliable securement. The cloth-like, flexible mechanical fastener may be of particular use in combination with disposable absorbent articles to secure the article about a wearer.

42 Claims, 8 Drawing Sheets

U.S. PATENT DOCUMENTS

| | | |
|---|---|---|
| 5,180,534 A | 1/1993 | Thomas et al. |
| 5,192,606 A | 3/1993 | Proxmire et al. |
| 5,226,992 A | 7/1993 | Morman |
| 5,231,738 A | 8/1993 | Higashinaka |
| 5,326,612 A * | 7/1994 | Goulait ............... 428/100 |
| 5,336,545 A | 8/1994 | Morman |
| 5,369,852 A | 12/1994 | Higashinaka |
| 5,369,853 A | 12/1994 | Okawa et al. |
| 5,401,275 A | 3/1995 | Flug et al. |
| 5,441,687 A | 8/1995 | Murasaki et al. |
| 5,473,800 A | 12/1995 | Hatomoto et al. |
| 5,509,915 A | 4/1996 | Hanson et al. |
| 5,515,583 A | 5/1996 | Higashinaka |
| 5,518,795 A * | 5/1996 | Kennedy et al. ......... 425/129.1 |
| 5,531,732 A * | 7/1996 | Wood ................. 604/391 |
| 5,545,159 A * | 8/1996 | Lancaster et al. ........ 604/391 |
| 5,554,146 A | 9/1996 | Niederhofer et al. |
| 5,606,781 A | 3/1997 | Provost et al. |
| 5,624,429 A * | 4/1997 | Long et al. ............ 604/391 |
| 5,669,901 A | 9/1997 | LaFortune et al. |
| 5,695,868 A | 12/1997 | McCormack |
| 5,744,080 A | 4/1998 | Kennedy et al. |
| 5,759,181 A | 6/1998 | Sayama et al. |
| 5,766,723 A | 6/1998 | Oborny et al. |
| 5,782,819 A | 7/1998 | Tanzer et al. |
| 5,786,061 A | 7/1998 | Banfield |
| 5,789,065 A | 8/1998 | Haffner et al. |
| 5,843,056 A | 12/1998 | Good et al. |
| 5,846,262 A | 12/1998 | Sayama et al. |
| 5,851,205 A | 12/1998 | Hisada et al. |
| 5,868,987 A * | 2/1999 | Kampfer et al. ............ 264/280 |
| 5,876,531 A | 3/1999 | Jacobs et al. |
| 5,897,545 A | 4/1999 | Kline et al. |
| 5,930,875 A | 8/1999 | Schreiner |
| 5,942,177 A | 8/1999 | Banfield |
| 5,957,908 A | 9/1999 | Kline et al. |
| 6,007,527 A | 12/1999 | Kawaguchi et al. |
| 6,030,373 A | 2/2000 | VanGompel et al. |
| 6,102,901 A * | 8/2000 | Lord et al. ............. 604/386 |
| 6,131,251 A * | 10/2000 | Provost ................ 24/452 |
| 6,149,934 A | 11/2000 | Krzysik et al. |
| 6,210,389 B1 * | 4/2001 | Long et al. ............ 604/391 |
| 2003/0004490 A1 * | 1/2003 | Larsson et al. .......... 604/390 |

* cited by examiner

CLOTH-LIKE MECHANICAL FASTENER

FIELD OF THE INVENTION

The present invention relates to a mechanical fastener suitable for use on a disposable absorbent article. More particularly, the present invention relates to a cloth-like mechanical fastener having improved flexibility and to methods by which such a fastener can be made.

BACKGROUND OF THE INVENTION

It is desired that mechanical fasteners have the ability to provide reliable yet comfortable securement of garments. Moreover, it is desirable that such mechanical fasteners be provided on a flexible material. The fastening material is desirably embedded within the flexible material to help present a cloth-like surface to the wearer or the caregiver and to reduce the possibility of the fastener having exposed harsh edges. In certain circumstances, it is also desirable that such fasteners include multiple discrete areas of mechanical fastening material to further enhance the flexibility of the fastener and reduce the possibility of creasing the rigid fastener material. This is particularly useful if the fastener is being used in combination with a garment to be worn by an active wearer. As such, it is desirable that the fastener be capable of being bent or conformed to better accommodate an active wearer while reducing the potential of creasing the rigid fastener material in order to avoid the creation of harsh, rough edges. In such circumstances, it is also desirable for the perimeter of the mechanical fastening material to be surrounded by the flexible material to further ensure the comfort of the wearer when the mechanical fastener is in use. Such fasteners can be advantageously provided for use on absorbent articles such as diapers, diaper pants, training pants, incontinence garments, feminine hygiene products, wound dressings or the like.

In general, the term "mechanical fasteners" may include hooks, snaps, buttons, zippers and other means. Specifically, the "mechanical fasteners" of subject invention are what are commonly referred to as "hook-and-loop" fastener systems. Some hook-and-loop systems employ hooks attached to a non-woven, woven, or knitted fabric backing. These systems, with hooks attached to a fabric backing find utility in various textile and durable applications, may be flexible, but are generally rather harsh and are too expensive for use in disposable absorbent products. More specifically, the focus of this invention is on hook-and-loop fastener systems wherein the "hooks" are directly attached to a more or less continuous polymer film or billet.

Typically, mechanical fasteners do not have a flexible backing material. Mechanical fasteners have conventionally had relatively thick and rigid backing materials that are prone to creasing. The creases, in combination with the harsh edges of the fastener material itself, may lead to red-marking or irritation of the wearer's skin. For example, mechanical fasteners currently used on absorbent articles typically include a single area of fastening material with a backing material that is several times thicker than the material used for the outer cover of the absorbent article. Typically, the outer cover film material is 10 to 20 µm thick. The backing material of mechanical fasteners is typically in the range of from about 50 to about 300 µm thick. Moreover, the mechanical fastening material is not recessed within the film backing material, thereby exposing the rigid edges of the fastening material.

In the past, absorbent articles have been constructed to include isolated areas or patches of hook fastening material for securement within the article itself or for securement of the article to a garment. While the hook fastening material of such articles may have been configured into discrete areas, the hook fastening material was not recessed around its edges into the surrounding material (such as a nonwoven material). Therefore, such articles still had the potential for harsh edges of fastening material to be exposed. The existing art has also recognized the need to somehow buffer the edges of hook fastening materials. For example, fastening materials having a base with feathered selvedge edges have been described. The thickness of the base gradually decreases from a nominal value to a minimum value over the width of the feathered selvedge edges. Such art, however, does not describe recession of the base edges into a surrounding material.

Accordingly, there remains a need for hook and loop type mechanical fastener systems that can provide the benefits of flexibility, softness, simplicity of manufacture and a cloth-like presentation. That is, there remains a need for mechanical fasteners that are provided on a flexible layer, that have the rough edges of the fastener material recessed within a flexible layer, and that can be bent or altered with reduced creasing. Such a fastener would improve the comfort of the wearer by better accommodating the wearer and providing a pleasing cloth-like feel in use. Moreover, there is a need for improved methods of reliably and consistently making disposable absorbent articles with such mechanical fasteners.

SUMMARY OF THE INVENTION

In response to the difficulties and problems discussed above, new mechanical fasteners, and methods by which fasteners can be made have been discovered. The mechanical fasteners of the present invention provide several benefits including a more cloth-like presentation, decreased likelihood of creasing and reduced risk of skin irritation. While the fasteners of the present invention can have a variety of applications, the fasteners are particularly beneficial when used in conjunction with absorbent articles such as diapers, incontinence garments, training pants and diaper pants. The purposes and advantages of the present invention will be set forth in and apparent from the description that follows, as well as will be learned by the practice of the invention. Additional advantages of the invention will be realized and attained by the fasteners and methods particularly pointed out in the written description and claims hereof, as well as from the appended drawings.

In one aspect, the present invention concerns a mechanical fastener that defines a fastener longitudinal direction, a fastener lateral direction, and a third direction. The fastener longitudinal direction is the direction that is parallel to the centerline of an absorbent article when a fastener is attached to an absorbent article and generally corresponds to the "y" direction of the fastener. The fastener lateral direction is the direction that is perpendicular to the centerline of an absorbent article when a fastener is attached to an absorbent article and generally corresponds to the "x" direction of the fastener. The third direction is the direction that is perpendicular to the plane defined by both the fastener lateral direction and the fastener longitudinal direction, and generally corresponds to the "z" direction of the fastener. The fastener comprises a flexible layer and at least one discrete fastener island. The fastener island has a planar perimeter edge, a mechanical fastening material, and a backing material attached to the mechanical fastening material. The backing material is embedded within the flexible layer and the planar perimeter edge is surrounded by the flexible layer. The planar perimeter edge is the outermost edge of the fastener island along a plane defined by the lateral and longitudinal direction, and is perpendicular to the third direction. As such, the planar perimeter edge defines the edge of the fastener island at its largest cross section.

The flexible layer may be constructed of a fabric, for example, a nonwoven material. Other suitable materials for the flexible layer include knit or woven fabrics, foams and reticulated films. Various types of nonwoven materials may be advantageously used as the flexible layer, such as a thermally or chemically bonded carded web or a nonwoven laminate. Examples of nonwoven laminates that may be advantageously used as the flexible layer include stretchable neck bonded laminates, such as those disclosed in U.S. Pat. No. 5,789,065 issued on Aug. 4, 1998 to Haffner et al. and U.S. Pat. No. 5,336,545 issued on Aug. 9, 1994 to Morman. Alternatively, relatively inelastic nonwoven laminates, such as a spunbond/meltblown/spunbond composite may also be advantageously used. When the flexible layer is provided by a nonwoven material, the flexible layer is generally soft to the touch and provides a cloth-like sensation to the wearer and the caregiver, as nonwoven materials are desirably comprised of fine fibers. The flexible layer may be extensible or stretchable, meaning that the layer is capable of extending to a greater length or width upon application of a force. Moreover, the flexible layer may define a particular thickness in the third direction, for example from about 250 to about 2500 $\mu$m.

The mechanical fastening material may consist of a hook material, and further, the hook material may contain multiple hooks. For example, the hook material may contain at least 20 hooks. The number of hooks can also be described in terms of a hook density (number of hooks per square centimeter). It is possible to fabricate hook material having a hook density of from about 60 hooks/cm$^2$ to about 1600 hooks/cm$^2$. More desirably, the hook material has a hook density of from about 100 hooks/cm$^2$ to about 750 hooks/cm$^2$. The term "hook" should be understood to encompass various geometries of protuberances that are suitable for engaging into a loop material or a material having loop characteristics in order to place or secure a fastener. Exemplary geometries include prongs, stems, trees (such as the shapes connoted by "evergreen" and "palm" trees), mushrooms, J-hooks, bi-directional hooks and studs protruding at various angles. In addition to the various possible geometries of hooks, the hooks may protrude from a backing material at various angles. U.S. Pat. No. 5,782,8199 issued to Tanzer et al. on Jul. 21, 1998 describes a fastener system that includes velvet fabrics as examples of materials exhibiting differential friction. The surface of velvet fabric has fibers protruding from the surface, oriented on a bias. Despite the fibers being essentially straight (i.e. without barbs or hooks), they engage an opposed surface and facilitate fastening. The discrete hooks of the hook material may include or be treated with materials such as soft rubbers that increase the coefficient of friction of the hooks against the corresponding loop/engaging material. The increased coefficient of friction serves to reduce the tendency of the fastener to pop-open under stress. The benefits of fasteners having increased coefficients of friction are described in U.S. patent application Ser. No. 09/705,512 entitled "Hook and Loop Fastener Having an Increased Coefficient of Friction" filed by Martin et al. on Nov. 3, 2000.

The backing material attached to the fastening material may be embedded in the flexible layer by ultrasonic or thermal bonds or by adhesive. In addition, the fastener may include a plurality of discrete fastener islands.

Further, the flexible layer of the mechanical fastener may include a first flexible layer and a second flexible layer. The first flexible layer may define an interior surface and an exterior surface where the backing material of the fastener island can be attached to the interior surface of the first flexible layer. The second flexible layer is also attached to the interior surface of the first flexible layer where the second flexible layer defines an opening that corresponds to the discrete fastener island and exposes the mechanical fastening material of the discrete fastener island. Accordingly, the first and second flexible layers are stacked flush upon each other in the third direction, with the second flexible layer providing an opening through which the mechanical fastening material of the discrete fastener island is exposed.

Finally, the mechanical fastener may also have a user's end and a bond end. The bond end can be permanently attached to a disposable absorbent article and the user's end contains the discrete fastener island. The user's end can also be configured to secure the disposable absorbent article about a wearer.

In another aspect, the present invention concerns a mechanical fastener that defines a fastener longitudinal direction, a fastener lateral direction, and a third direction. The fastener also includes a nonwoven layer and a plurality of discrete fastener islands. The discrete fastener islands have a planar perimeter edge, a mechanical fastening material and a backing material attached to the mechanical fastening material. The backing material of each of the discrete fastener islands is embedded within the nonwoven layer and the planar perimeter edge of each of the discrete fastener islands is surrounded by the nonwoven layer.

The planar perimeter edges of the plurality of fastener islands may have various shapes, such as circular. Other suitable shapes may include, but are not limited to, square, triangular, oval, linear, and the like, or combinations thereof. The nonwoven layer may be provided by a variety of nonwoven materials such as a thermally or chemically bonded carded web, a nonwoven or a laminate of nonwovens including neck bonded laminates, as well as spunbond/meltblown/spunbond composites. The nonwoven layer may be extensible or stretchable as described previously. Moreover, the nonwoven layer may define a particular thickness in the third direction, for example from about 250 to about 2500 $\mu$m.

As with the previously described aspect of the invention, the mechanical fastening material may consist of a hook material, and further, the hook material may contain multiple hooks. For example, the hook material may contain at least 20 hooks. In addition, the hook material may be constructed of flat top hook material. The backing material attached to the fastening material may be embedded in the flexible layer by ultrasonic bonds.

Further, the nonwoven layer of the mechanical fastener of this aspect of the invention may include a first nonwoven layer and a second nonwoven layer. The first nonwoven layer may define an interior surface and an exterior surface where the backing material of the discrete fastener islands can be attached to the interior surface of the first nonwoven layer. The second nonwoven layer is attached to the interior surface of the first nonwoven layer where the second nonwoven layer defines an opening that corresponds to the discrete fastener islands and exposes the mechanical fastening material of the discrete fastener islands. Accordingly, the first and second nonwoven layers are stacked flush upon each other in the third direction, with the second nonwoven layer providing openings through which the mechanical fastening material of the discrete fastener islands are exposed.

Finally, the mechanical fastener may also have a user's end and a bond end. The bond end can be permanently attached to a disposable absorbent article and the user's end contains the discrete fastener islands. Accordingly, as the user's end contains the fastener islands, the user's end is configured to secure the disposable absorbent article about a wearer. Alternatively, the mechanical fastener may be integral to the absorbent article; that is, the flexible layer of the mechanical fastener may be an extension of the outer cover, bodyside liner or other component of the main body of the absorbent article. An example would be an absorbent article that includes an integral belt element. The ends of the belt element may include the flexible layer of the mechanical fastener. In another alternative, the mechanical fastener may be located on an attachment panel in either a front or rear waist portion of the absorbent article. A loop or other engaging material is then located integral with or attached to the outer cover. The loop material is located on a portion of the article that extends laterally away from the longitudinal centerline of the article. The loop material portion or portions are then wrapped around the waist of the wearer so as to engage the mechanical fastener located on the attachment panel of the article.

The number and configuration of fastener islands on the fasteners of the invention can vary. A moderate number of fastener islands on a fastener can range from to 2 to about 16; a large number of fastener islands on a fastener would be a number greater than about 16. In addition to the number of fastener islands, the total hook area accumulated by the fastener islands will affect the cost, flexibility, grip, skin friendliness and ease of manufacture of the fasteners. A low hook area is an area of about $2 \text{ cm}^2$ or less; a high hook area is an area of about $8 \text{ cm}^2$ or more; a moderate hook area is an area between about $2 \text{ cm}^2$ and about $8 \text{ cm}^2$. Having a relatively low number of islands combined with a low hook area provides a fastener having low manufacturing cost, high flexibility, low grip and skin friendliness. Increasing the hook area to a moderate hook area increases the cost and improves the grip of the fastener; using a high hook area with a low number of islands would have a further increased cost. Having a relatively large number of islands combined with a low hook area provides a fastener having low manufacturing cost, high flexibility, low grip and skin friendliness but also being relatively more difficult to manufacture at high speeds. Increasing the hook area to a moderate hook area increases the cost and improves the grip of the fastener; using a high hook area with a large number of islands would have an even higher cost and could have decreased skin friendliness. Based on a balancing of the relevant factors, it is desirable for a fastener to have a relatively low number of fastener islands and a moderate total hook area (the area of hooks not including the "sea" areas between the fastener islands). Such fasteners provide the benefits of moderate cost, high flexibility, strong grip and skin friendliness.

The spacing between fastener islands can range from about 3 mm to about 30 mm. The fastener islands can be arranged in any suitable geometry including a "checkerboard" pattern, a chevron pattern and around the perimeter of an oval or other shape. For some fasteners, it may be desirable to arrange the fastener islands to create well-defined lines of flexibility by leaving "lines" free of fastener islands. For other fasteners, it may be desirable to arrange the fastener islands to block lines of flexibility.

In yet another aspect, the present invention concerns a disposable absorbent article that includes an outer cover, a bodyside liner, an absorbent core located between the bodyside liner and the outer cover, and at least one mechanical fastener. The mechanical fastener includes a nonwoven layer and a plurality of discrete fastener islands. The discrete fastener islands have a planar perimeter edge and a mechanical fastening material. A backing material is attached to the mechanical fastening material. The backing material of each of the discrete fastener islands is embedded within the nonwoven layer and the planar perimeter edge of the discrete fastener islands is surrounded by the nonwoven layer. The mechanical fastener is configured to refastenably secure the disposable absorbent article about a wearer.

The mechanical fastening material of the fastener on the disposable absorbent article may be a variety of fastening materials including a hook material. In addition, the mechanical fastener can be configured to refastenably engage directly to the outer cover of the absorbent article. Alternatively, the disposable absorbent article can also include an attachment panel, where the fastener is configured to refastenably engage the attachment panel. Conversely, the fastener can be located on the attachment panel and can be configured to refastenably engage another portion of the article having a complementary engagement material.

In still another aspect, the present invention concerns a fastener made by a process including the step of providing a continuous nonwoven web. This is followed by a step of intermittently applying drops of a molten polymer to the nonwoven web. Suitable polymers include polypropylene, and other polyolefins, nylons, aromatic and aliphatic polyesters including polylactic acid-based polymers, polyurethanes, natural and synthetic rubbers, proteins and other polymers. The process continues with a step of molding the drops of molten polymer into a plurality of discrete fastener islands to provide a backing material and a mechanical fastening material in each of said discrete fastener islands. The process concludes with a step of chilling the discrete fastener islands, and embedding the backing material within the nonwoven web to provide a continuous web of mechanical fasteners. The molten polymer may be molded and chilled by using a combination of a rotary die and a pressure roller. The rotary die may be configured to mold the molten polymer while being internally cooled to chill the molten polymer, thereby embedding it within the nonwoven web.

The mechanical fastening material of the mechanical fastener produced by this process can be hook fastening material. Moreover, the nonwoven web can be a neck bonded laminate web or a thermally bonded carded web. Further, the mechanical fasteners produced by the process described above may be configured to be nested within an adjacent fastener in the continuous web of mechanical fasteners. U.S. Pat. No. 5,876,531 issued to Jacobs et al. on Mar. 2, 1999 describes such a process for making mechanical fasteners. Accordingly, in such a configuration, the fasteners fit within the negative space created when the adjacent fastener is cut from the nonwoven web without any wasted nonwoven materials. Finally, the mechanical fastener may also be produced by a process that further includes the step of cutting individual fasteners from the continuous web of mechanical fasteners or the process could further include the step of winding the continuous web of fastener.

The present invention advantageously provides cloth-like mechanical fasteners and methods by which cloth-like mechanical fasteners can be made. In particular, the present invention includes mechanical fasteners that provide reliable securement of absorbent articles upon a wearer while still being flexible and providing a cloth-like presentation to the wearer and others coming into contact with the fasteners. Moreover, the mechanical fasteners of the present invention provide a mechanical fastening area that is recessed within the flexible layer, reducing the possibility of exposing any rigid edges of the fastening material that may be present. In addition, due to the refastenable nature of the fasteners of the present invention, the fasteners may be applied and re-applied to adjust and improve the fit of the article upon the wearer. Moreover, skin irritation in the user of the fastener during repeated application and reapplication of the fasteners may be reduced, because the embedding of the fastener islands shields the user and the wearer from the potentially harsh fastening material. Accordingly, wearer and caregiver comfort is enhanced. Reducing the occurrence and severity of skin irritation on areas of skin covered by absorbent articles or other sensitive areas is particularly important as the skin in these areas are more susceptible to the discomfort of inflammation. In certain configurations, the mechanical fastener of the present invention is particularly capable of being bent or conformed without producing harsh creases in the mechanical fastening material. This flexibility heightens the soft, cloth-like presentation of the fastener of the present invention to the wearer and the caregiver. Moreover, this flexibility also provides improved fit and comfort to the wearer by allowing the fastener to better conform to the body of the wearer and better accommodating the movement of the active wearer.

An additional benefit of a fastener that more closely conforms to the body of the wearer is more reliable fastening. It is often desirable to provide a soft and flexible loop portion as part of a hook and loop fastening system. When using a soft and flexible loop portion, the hook portion of the fastener is desirably selected so as not to compromise the security of the fastening system. If the hook and loop portions are mismatched, the softer portion will gently fold when subjected to external forces and the more rigid portion may form sharp creases. When this occurs, the external forces tend to pull the hooks away from the loops leading to failure (a.k.a. "pop opens"). The soft, flexible hook portions of the present invention are more suitably matched with soft, flexible loop portions to provide improved security. Thus, the fastener of the present invention improves the fit and comfort of the garment, and additionally reduces the occurrence of irritation and red-marking of the wearer's skin.

An additional benefit of the present invention is that the cloth-like presentation of the fastener provides opportunities for improved aesthetics. The flexible layer may be printed with any desired pattern and the fastener islands may be colored in such a way that they either blend with or contrast with the flexible layer. When the fastener islands visually contrast with the flexible layer, they can be arranged to give an attractive geometric or cartoon-like impression.

It is understood that both the foregoing general description and the following detailed description are exemplary and are intended to provide further explanation of the invention claimed. The accompanying drawings, which are incorporated in and constitute part of this specification, are included to illustrate and provide a further understanding of the fasteners and processes for making fasteners of the present invention. Together with the description the drawings serve to explain the various aspects of the invention.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention is directed to solving the problems related to the comfort and fit of garments having mechanical fasteners. For example, the present invention is directed to solving the potential problem of skin irritation that may result from the rigidity of the backing material of conventional mechanical fasteners. Moreover, the present invention is directed to solving the problem of potential skin irritation that may be caused by the fastening material of the fastener itself. Further, the present invention is directed to solving the possible problems related to the fit and comfort of conventional mechanical fasteners. For example, the rigidity of conventional mechanical fasteners limit the range of application of the fastener, which in turn, may impair the wearer of the garment from achieving optimal fit of the garment. In addition, conventional mechanical fasteners may not accommodate an active wearer in the full range of motion at the junction of the hip and leg of the wearer.

The present invention encompasses a mechanical fastener, particularly for use on a disposable absorbent article, and processes by which mechanical fasteners can be made. The mechanical fasteners are configured to provide a cloth-like presentation to the wearer and the caregiver. When in use with a disposable absorbent article, the mechanical fasteners of the present invention are configured to secure the disposable absorbent article about a wearer. Accordingly, the absorbent articles employing the mechanical fasteners of the present invention are configured to closely conform to the body of the wearer to effectively contain body exudates. In addition, the mechanical fasteners of the present invention are refastenable so that absorbent articles using them may be secured to and removed directly from the waist of the wearer and easily inspected to determine if they have been soiled during use. As used herein, the term "cloth-like" refers to materials, and components incorporating such materials, that provide a soft, compliant, and generally pleasing sensation to those coming in contact with it, similar to clothing. As used herein, the term "disposable" refers to articles that are intended to be discarded after a limited use and which are not intended to be laundered or otherwise restored for reuse.

The cloth-like mechanical fastener of the present invention will be described in terms of being used in combination with a disposable diaper article that is adapted to be worn by infants about the lower torso. It is understood that the fasteners and methods of the present invention are equally adaptable for other types of absorbent articles such as adult incontinent products, training pants, feminine hygiene products, other personal care or health care garments, diaper pants and similar types of articles.

Figure 1:
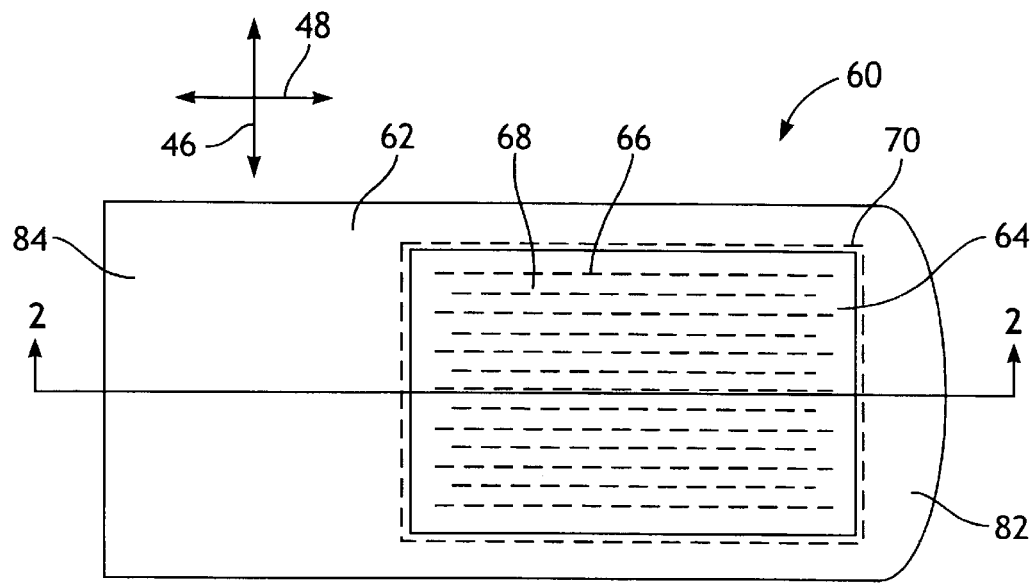
FIG. 1 representatively illustrates a top plan view of an example of a mechanical fastener of the present invention.

FIG. 1 representatively illustrates an example of a cloth-like mechanical fastener, as generally indicated at 60, of the present invention. As illustrated in FIG. 1, the fastener 60 comprises a flexible layer 62 and a fastener island 64. The fastener island 64 has a planar perimeter edge 70, a mechanical fastening material 66 and a backing material 68 attached to the mechanical fastening material 66. The fastener 60 may also define a users end 82, a manufacturer's bond end 84, a fastener longitudinal direction 46, and a fastener lateral direction 48. As used herein, the term "fastener longitudinal direction" means the direction that is parallel to the centerline of an absorbent article when a fastener 60 is attached to an absorbent article and generally corresponds to the "y" direction of the fastener 60. As used herein, the term "fastener lateral direction" means the direction that is perpendicular to the centerline of an absorbent article when a fastener 60 is attached to an absorbent article and generally corresponds to the "x" direction of the fastener 60. As used herein, the term "third direction" means the direction that is perpendicular to the plane defined by the fastener lateral direction and the fastener longitudinal direction, and generally corresponds to the "z" direction of the fastener 60. As used herein, the term "planar perimeter edge" means the outermost edge of the fastener island 64 along a plane defined by the lateral 48 and longitudinal direction 46, and is perpendicular to the third direction 52. As such, the planar perimeter edge 70 defines the edge of the fastener island 64 at its largest cross section.

The illustrated mechanical fastener 60 of the present invention includes a flexible layer 62. The flexible layer 62 generally provides the chassis for the fastener 60. The flexible layer 62 desirably provides a feeling of flexibility and softness to the wearer. The flexible layer 62 may be provided by a variety of materials as are well known to those skilled in the art. For example, the flexible layer 62 may be provided by knits, wovens, fabrics, papers, foams, reticulated films, nonwovens, and similar materials, or combinations thereof. Various types of nonwoven materials may be advantageously used as the flexible layer 62, such as a thermally or chemically bonded carded web or a nonwoven laminate. Examples of nonwoven laminates that may be advantageously used as the flexible layer 62 include stretchable neck bonded laminates, such as those disclosed in U.S. Pat. No. 5,789,065 issued on Aug. 4, 1998 to Haffner et al. and U.S. Pat. No. 5,336,545 issued on Aug. 9, 1994 to Morman. Alternatively, relatively inelastic nonwoven laminates, such as a spunbond/meltblown/spunbond composite may also be advantageously used. Desirably, the flexible layer 62 is provided by a nonwoven such as a neck bonded laminate or a thermally bonded carded web (hereinafter "TBCW"). In particular, it is desirable that the fibers of the flexible layer 62 be sufficiently fine such that the flexible layer 62 is accordingly soft to the touch.

Figure 2:
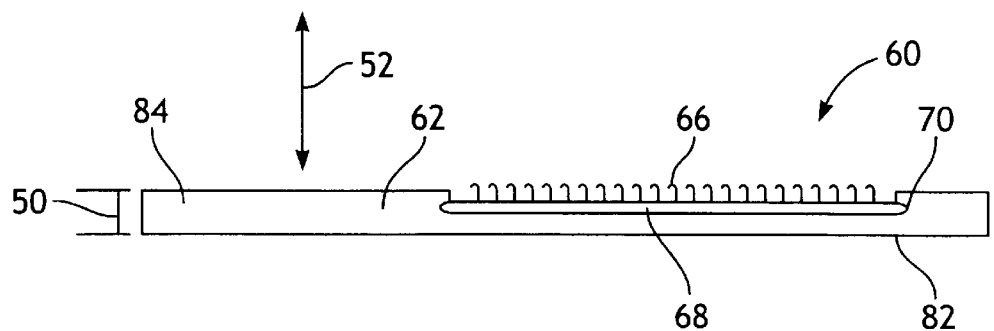
FIG. 2 representatively illustrates a section view of the mechanical fastener of FIG. 1 along line A—A.
Figure 3:
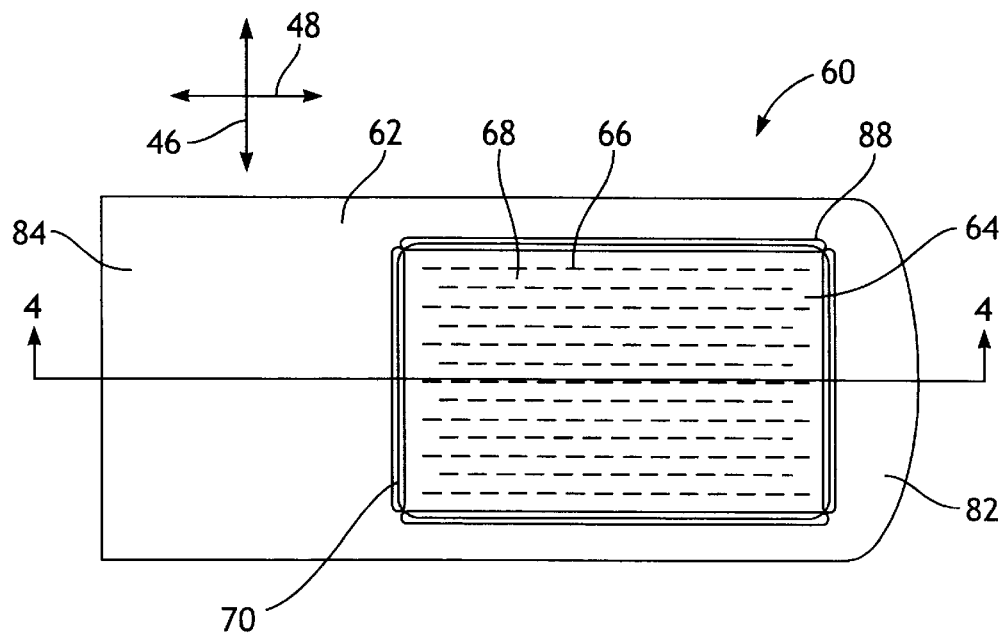
FIG. 3 representatively illustrates a top plan view of another example of a mechanical fastener of the present invention wherein the fastener island is attached to the flexible layer via ultrasonic bonds.
Figure 4:
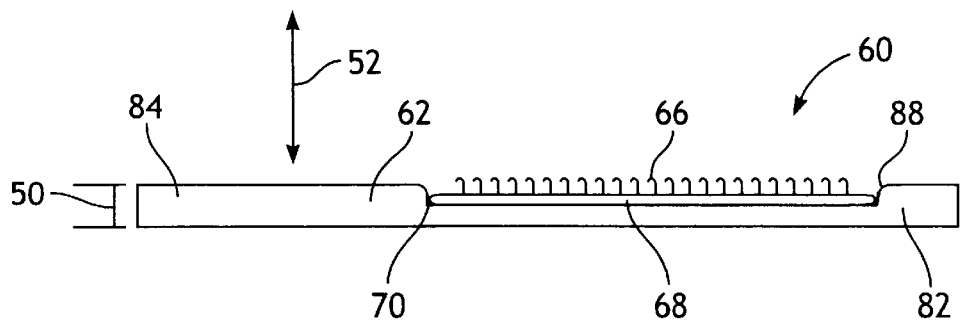
FIG. 4 representatively illustrates a section view of the mechanical fastener of FIG. 3 along line A—A.
Figure 6:
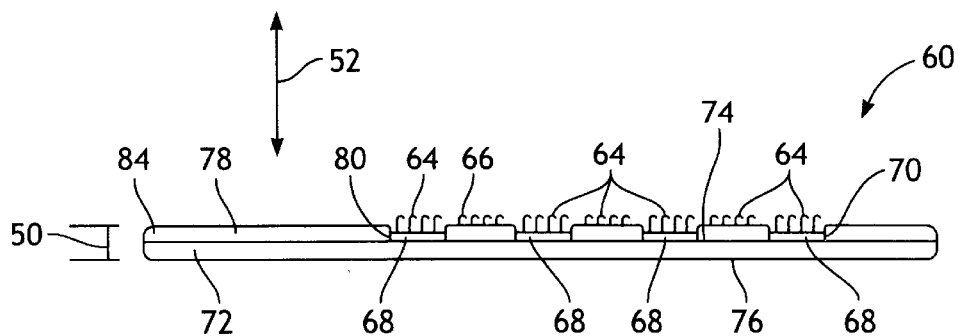
FIG. 6 representatively illustrates a section view of the mechanical fastener of FIG. 5 along line A—A.

As representatively illustrated in FIGS. 2, 4 and 6, the fastener 60 also defines a fastener thickness 50 in a third direction 52. The flexible layer 62 of the fastener 60 of the present invention defines a fastener thickness 50 which is generally smaller than the thickness of the chassis of fasteners known in the art. Desirably, however, the total fastener thickness 50 of the flexible layer 62 remains generally greater than the thickness of the fastener island 64 in the third direction 52. In particular, the flexible layer 62 may define a fastener thickness 50 of from about 250 μm to about 2500 μm. More particularly, the flexible layer 62 may define a fastener thickness 50 of from about 400 μm to about 1600 μm. Yet even more particularly, the flexible layer 62 may define a fastener thickness 50 of from about 600 μm to about 1200 μm. In particular aspects, the fastener thickness 50 provided by the flexible layer 62 can be at least a minimum of about 250 μm. The fastener thickness 50 can alternatively be at least about 400 μm, and optionally, can be at least about 600 μm to provide improved performance. In other aspects the fastener thickness 50 provided by the flexible layer 62 can be not more than a maximum of about 2500 μm. The fastener thickness 50 can alternatively be not more than about 1600 μm, and optionally, can be not more than about 1200 μm to provide improved performance. As such, the flexible layer 62 maintains in the fastener 60 a desirable flexibility and drape to provide the wearer and the caregiver with the sensation softness and comfort, such as would be expected to be provided by a cloth-like material.

The flexible layer 62 of the fastener 60 generally provides the shape of the fastener 60. That is, the perimeter edge of the flexible layer 62 defines the profile or shape of the fastener 60. As such, the fastener 60 may have a variety of suitable shapes as are well known to those in the art. For example, as representatively illustrated in FIGS. 1–6 and 8, the fastener 60 may have a generally rectangular shape. Alternatively, the flexible layer 62 may provide the fastener 60 with a curvilinear shape that may improve the comfort of the wearer by better conforming to the contours of the wearer's body.

Desirably, the flexible layer 62 is extensible or elastic in at least the fastener longitudinal direction 46. For example, the flexible layer 62 may be comprised of a stretch-thermal laminate (STL) neck-bonded laminate (NBL), or stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., the disclosures of which are hereby incorporated by reference.

The flexible layer 62 may include a single piece of material or multiple pieces of material. For example, the flexible layer 62 may include multiple pieces of material in the fastener lateral direction 48. As such, the flexible layer 62 may include an extensible panel located between a pair of generally non-extensible flexible materials to provide a flexible layer 62 that is extensible, as described above. Alternatively, the flexible layer 62 may include multiple pieces of material that are arranged in layers in the third direction 52, as will be discussed in more detail below.

The mechanical fastener 60 of the present invention further includes at least one discrete fastener island 64. As representatively illustrated in FIGS. 1–5 the discrete fastener island 64 includes a mechanical fastening material 66 and a backing material 68 attached to the fastening material 66. The fastener island 64 also defines a planar perimeter edge 70. The planar perimeter edge 70 is the outermost edge of the fastener island 64 along a plane that is perpendicular to the third direction 52. As such, the planar perimeter edge 70 defines the edge of the fastener island 64 at its largest cross section.

The mechanical fastening material 66 of the discrete fastener island 64 allow the fastener 60 to refastenably engage the exterior surface 36 of the diaper 20 (shown in FIG. 8), thereby securing the diaper 20 about the wearer in use. Suitable fasteners to provide the fastening material 66 of the fastener islands 64 are well known to those skilled in the art and can include, hook and loop material, mushroom material, snaps, pins, and similar fastening material, and combinations thereof. Desirably, in one aspect, the fastening material 66 of the fastener island 64 is a hook type fastener material. As such, the fastener island 64 may contain multiple hooks. For example, as representatively illustrated in FIGS. 1–6 and 9, the fastening material 66 of each of the fastener islands 64 provides multiple hooks. In particular, the fastening material 66 of each of the fastener islands 64 may contain at least about 20 hooks.

The number of hooks can also be described in terms of a hook density (number of hooks per square centimeter). It is possible to fabricate hook material having a hook density of from about 60 hooks/cm$^2$ to about 1600 hooks/cm$^2$. More desirably, the hook material has a hook density of from about 100 hooks/cm$^2$ to about 750 hooks/cm$^2$. The term "hook" should be understood to encompass various geometries of protuberances that are suitable for engaging into a loop material or a material having loop characteristics in order to place or secure a fastener. Exemplary geometries include prongs, stems, trees (such as the shapes connoted by "evergreen" and "palm" trees), mushrooms, J-hooks, bi-directional hooks and studs protruding at various angles. In addition to the various possible geometries of hooks, the hooks may protrude from a backing material at various angles. U.S. Pat. No. 5,782,8199 issued to Tanzer et al. on Jul. 21, 1998 describes a fastener system that includes velvet fabrics as examples of materials exhibiting differential friction. The surface of velvet fabric has fibers protruding from the surface, oriented on a bias. Despite the fibers being essentially straight (i.e. without barbs or hooks), they engage an opposed surface and facilitate fastening. The discrete hooks of the hook material may include or be treated with materials such as soft rubbers that increase the coefficient of friction of the hooks against the corresponding loop/engaging material. The increased coefficient of friction serves to reduce the tendency of the fastener to pop-open under stress. The benefits of fasteners having increased coefficients of friction are described in U.S. patent application Ser. No. 09/705,512 entitled "Hook and Loop Fastener Having an Increased Coefficient of Friction" filed by Martin et al. on Nov. 3, 2000.

Figure 7:
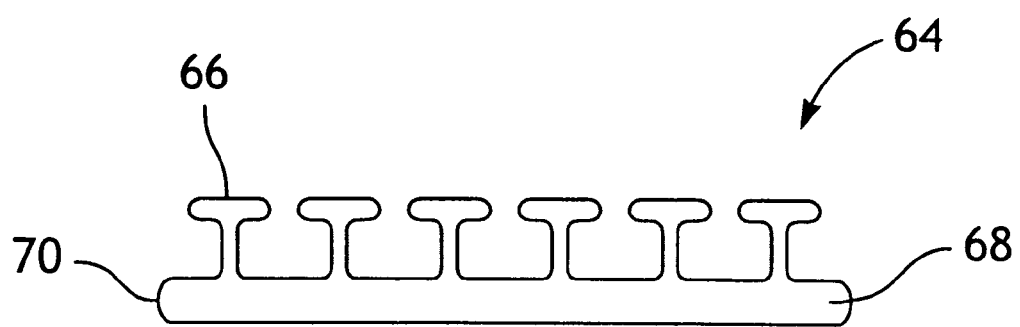
FIG. 7 representatively illustrates an elevation view of an example of the fastener island of the present invention.

When the mechanical fastening material 66 of the fastener island 64 is provided by hook material, different hook configurations may be provided. For example, as representatively illustrated in FIG. 7, the fastening material 66 may be provided by a flat top hook material. Flat top hook material advantageously presents a surface that is less likely to expose the wearer to any coarse, sharp edges and provides a more smooth feeling fastener surface. As such, the flat top hook material provides a fastening material 66 that may reduce the possibility of irritation and discomfort to the wearer and/or the caregiver. In addition, the flat top hook material advantageously provides reliable engagement with the exterior surface 36 of the diaper 20, ensuring that the mechanical fasteners 60 will dependably refastenably secure the diaper 20 about the waist of a wearer, as will be described in greater detail below.

The fastener islands 64 of the present invention also include a backing material 68 that is attached to the fastening material 66. The backing material 68 of the fastener islands 64 is embedded within the flexible layer 62 of the fastener. By embedding the backing material 68 of the fastener islands 64 within the flexible layer 62, the present invention provides the wearer with a more cloth-like fastener in that there is a reduced possibility of irritation and discomfort because the rigid edges of the fastener island 64 are recessed within the flexible layer 62. As such, the embedding of the backing material 68 of the fastener islands 64 also ensures that the planar perimeter edge 70 of the fastener island 64 is surrounded by the flexible layer 62. Accordingly, the only portion of the fastener island 64 that is exposed above the surface of the flexible layer (in the "z" direction) is the fastener material 66. This configuration ensures that the fastener 60 is able to provide a cloth-like presentation and reduces the possibility of irritation and discomfort to the wearer.

The fastener islands 64 may be embedded within the flexible layer 62 in a variety of ways. For example, as representatively illustrated in FIGS. 1–2, the fastener island 64 may be provided by applying molten polymer to the flexible layer 62. The drops of molten polymer may then be molded into a discrete fastener island 64. As such, during the molding process, some of the polymer may impregnate a discrete section of the nonwoven web forming the backing material 68 of the fastener island 64, while some other portion of the polymer is molded into the mechanical fastening material 66 of the fastener island 64. For example, the mechanical fastening material 66 may be molded into hooks. The molten polymer may then be chilled, providing a flexible layer 62 with the backing material 68 of the fastener island 64 embedded therein.

Figure 5:
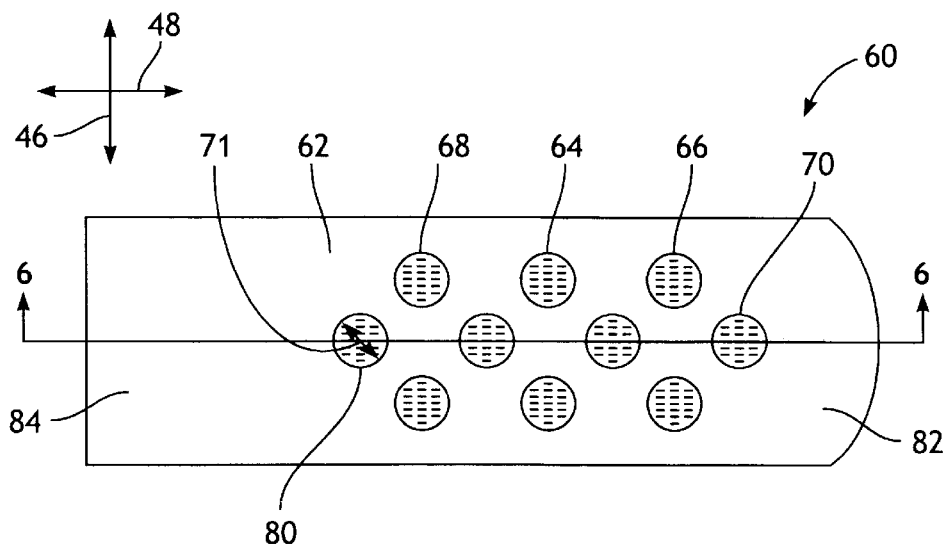
FIG. 5 representatively illustrates a top plan view of an alternate configuration of a mechanical fastener of the present invention having a plurality of fastener islands.

Alternatively, as representatively illustrated in FIGS. 5 and 6, the embedding of the fastener island 64 within the flexible layer 62 may be accomplished by providing the flexible layer 62 with multiple layers in the third direction 52. For example the flexible layer 62 may be comprised of a first flexible layer 72 and a second flexible layer 78. The first flexible layer 72 defines an interior surface 74 and an exterior surface 76 opposite the interior surface 74. The second flexible layer 78 can be attached to the interior surface 74 of the first flexible layer 72. Similarly the backing material 68 of the fastener island 64 is permanently attached to the first flexible layer interior surface 74. The second flexible layer 78 defines an opening 80 which corresponds to each of the fastener islands 64. The opening 80 in the second flexible layer 78 allows the mechanical fastening material 66 of the fastener island 64 to be exposed while the backing material 68 remains embedded within the second flexible layer 78.

In yet another alternative, the fastener islands 64 of the present invention may be embedded within the flexible layer 62 of the fastener 60 by ultrasonic bonds. For example, as representatively illustrated in FIGS. 3 and 4, the fastener island 64 is permanently attached to the flexible layer 62 using ultrasonic bonds 88. In particular, by using closely spaced ultrasonic bonds 88, the backing material 68 of the fastener island 64 becomes recessed within the flexible layer 62. For example, each fastener island 64 can have one or more bond points for holding it in place. Accordingly the fastener 60 may thereby provide a more cloth-like presentation that has a reduced possibility of irritating the wearer's skin.

In another aspect, the present invention includes fasteners 60 in which the flexible layer 62 is a soft, flexible foam with a density of less than about 0.4 g/cm$^3$. The fastener islands 64 are applied to the top surface of the flexible layer 62. The fastener islands 64 are sonically bonded to the flexible layer 62. During the process of sonic bonding, the foam of the flexible layer 62 is partially crushed, thereby reducing its thickness approximately in half and approximately doubling its density. Alternatively, the flexible layer 62 can include three or more layers. With the multiple-layered flexible layer 62 of the invention, there is a first flexible layer 72 having an interior surface 74 and an exterior surface 76. An adhesive is applied to the interior surface 74 of the first flexible layer 72. The backing material 68 of the fastener islands 64 is applied to the adhesive-coated interior surface 74. The backing material 68 can include flanges that extend laterally away from the positions of the individual hooks. Such flanges can serve to further anchor the backing material 68 to the first flexible layer 72. The flexible layer 62 further includes a second flexible layer 78 that has pre-cut holes or openings 80 that correspond to the locations of the fastener islands 64. The second flexible layer 78 is applied onto the first flexible layer 72 over the fastener islands 64. It is also possible for the flanges to extend between fastener islands 64 so that the fastener islands 64 are the intersections. In such an aspect, the first flexible layer 72 can be substantially thinner than the second flexible layer 78. For example, the first flexible layer 72 can include a spunbond layer having a basis weight of about 20 to about 40 g/m$^2$.

In another aspect of the invention, an adhesive can be applied to an exterior surface 76 of the second flexible layer 78. The fastener islands 64, with laterally extending flanges, are applied from underneath to the exterior surface 76. A first flexible layer 72 is formed by flocking fibers onto the remaining exposed adhesive on the exterior surface 76 of the second flexible layer 78. A soft, fuzzy first flexible layer 72 can be formed by blowing polyester staple or other fibers onto the adhesive.

The present invention also encompasses different heights above the flexible layer 62 that the mechanical fastening material 66 is exposed. Depending on the softness of the flexible layer 62, more or less of the mechanical fastening material 66 needs to be exposed. If the compression modulus of the flexible layer 62 is low (relative to how much force is used when the fastener 60 is applied during use), it is possible for the top of the mechanical fastening material 66 to be even with the "top" surface of the flexible layer 62. The greater the compression modulus of the flexible layer 62, the more of the mechanical fastening material 66 that must be exposed for adequate hook engagement. One advantage of having the top surface of the mechanical fastening material 66 even with the flexible layer 62 is that the fastener 60 would have a very gentle feel and any non-engaged portion of the mechanical fastening material that contacts skin would not have exposed hook members.

In a further aspect of the present invention, a more aggressive mechanical fastening material 66 is surrounded, as part of the fastener 60, by a less aggressive fastening material in the flexible layer 62. An example would be to use a hook material for the fastener islands 64 and to use a "velvet-like" material as the flexible layer 62. Examples of suitable "velvet-like" materials are disclosed in U.S. Pat. No. 5,782,819 issued to Tanzer et al. on Jul. 21, 1998.

The mechanical fastener island 64 may be provided in a variety of suitable shapes as are well-known to those skilled in the art. For example, as representatively illustrated in FIGS. 3 and 4, the fastener island 64 has a generally rectangular shape. Alternatively, as representatively illustrated in FIGS. 5 and 6, the fastener island 64 presents a generally circular shape. Other suitable shapes may include, but are not limited to, triangular, oval, linear, and the like, or combinations thereof. It is desirable to use a shape of mechanical fastener island 64 that does not have sharp edges and, if the mechanical fastener islands 64 are formed from a strip of material, to use a shape that "nests" so as to minimize material waste.

As described above, the mechanical fastener 60 of the present invention is provided with at least one fastener island 64 embedded within the flexible layer 62. Alternatively, as representatively illustrated in FIGS. 5 and 6 the fastener 60 may include a plurality of fastener islands 64. For example, as representatively illustrated in FIGS. 5 and 6 the mechanical fastener 60 includes multiple fastener islands 64. As such, the mechanical fastener 60 is provided with even greater flexibility. This increased flexibility is provided by having some flexible layer 62 material located between the multiple fastener islands 64. Therefore, a fastener with multiple fastener islands 64 is more flexible than a fastener that must be bent without multiple fastener islands 64. The backing material 68 is typically substantially stiffer than the nonwoven material typically used for the flexible layer 62. By breaking the mechanical fastener material 66 into discrete islands, the nonwoven material of the flexible layer 62 acts as a hinge. Moreover, since the multiple fastener islands 64 reduce the possibility of the user of the fastener 60 from creasing the backing material 68 of the fastener islands 64, the opportunity for the creation of harsh edges in the fastener 60 is reduced. Finally, the reduction of the possibility for harsh edges, which may develop in a traditional mechanical fastener in use, likewise reduces the opportunity for the fastener to red-mark or irritate the wearers skin.

The increased flexibility of the mechanical fastener 60 with multiple fastener islands 64 also allows the mechanical fastener 60 to be adjusted to a wider range of positions in use to achieve the optimum fastening location on the diaper 20 for improved fit and comfort. For example, a more flexible fastener may be capable of engaging the exterior surface 36 of the diaper 20 in a wider range of locations than a more rigid fastener. That is, the fastener 20 of the present invention is capable of being extended and bent more easily than a rigid mechanical fastener. A rigid mechanical fastener may have a more limited range of motion and thus a more limited area of engagement locations on the diaper 20. As such, a more flexible fastener such as the fasteners 60 of the present invention may be used to improve the fit and comfort of the wearer of the diaper 20 in use and thereby also reduce the opportunity for undesirable leakage. Moreover this added flexibility allows the fastener 60 to better accommodate the movement of the wearer in use.

In a particular embodiment, as representatively illustrated in FIGS. 5 and 6, the mechanical fastener 60 may include a plurality of generally circular discrete fastener islands 64. As such, the discrete fastener islands 64 may define a fastener island diameter 71. Desirably, the fastener island diameter 71 is from about 8 mm to about 32 mm. Even more desirably, the fastener island diameter 71 is from about 10 mm to about 28 mm, and still yet more desirably, the fastener island diameter 71 is from about 14 mm to about 20 mm. In particular aspects, the fastener island diameter 71 can be at least a minimum of about 8 mm. The fastener island diameter 71 can alternatively be at least about 10 mm, and optionally, can be at least about 14 mm to provide improved performance. In other aspects, the fastener island diameter 71 can be not more than a maximum of about 28 mm, and optionally, can be not more than about 20 mm to provide improved performance.

Figure 9:
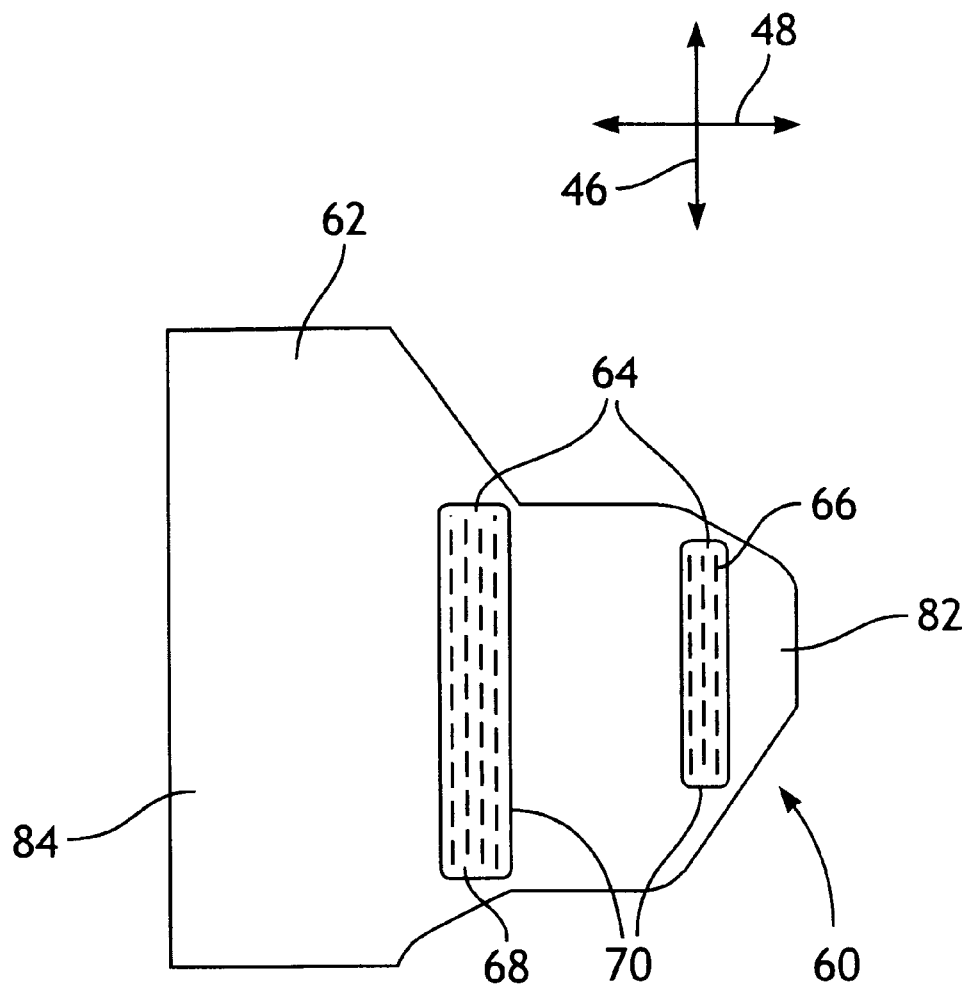
FIG. 9 representatively illustrates a top plan view of an alternate configuration of a mechanical fastener of the present invention having discrete fastener islands and a flexible layer that is extensible between the fastener islands.

In a particular aspect, as representatively illustrated in FIG. 9, the mechanical fastener 60 of the present invention may include a plurality of discrete fastener islands 64 where the flexible layer 62 is extensible between each of the fastener islands 64. Even more particularly, there may be a pair of fastener islands 64 that extend substantially along the entire fastener 60 in the fastener longitudinal direction 46, while yet being relatively narrow in the fastener lateral direction 48. Accordingly, this particular embodiment may be directed to a mechanical fastener 60 having a pair of fastener islands 64 that extend generally in the fastener longitudinal direction 46 and not as extensively in the fastener lateral direction 48, and having a flexible layer 62 which is extensible particularly between the fastener islands 64. This arrangement, when applied in a stretched configuration, acts to pull the fastener islands 64 together, thereby placing the mechanical fastener 60 in a shear mode of failure in use. As such, this particular embodiment advantageously provides a mechanical fastener 60 that is subjected primarily to shear forces when engaged upon the exterior surface 36 of a diaper 20. Typically, a fastener that is subjected primarily to shear forces provides more reliable securement than a fastener that is subjected primarily to peel forces in use. As such, the mechanical fastener 60 of this particular embodiment is capable of providing increased securement with a smaller amount of fastener material 66, thereby providing improved performance at a reduced material cost.

Still more particularly, the fastener islands 64 of this specific aspect of the mechanical fastener 60 described above may have a particular length in the fastener lateral direction 48. For example, the length of the fastener islands 64 in the fastener lateral direction 48 may desirably be from about 0.625 cm to about 2.54 cm. Even more desirably, the fastener islands 64 may have a length in the fastener lateral direction 48 of about 0.95 cm. In particular aspects, the length of the fastener island 64 in the fastener lateral direction 48 can at least be a minimum of about 0.625 cm. In other aspects, the length of the fastener island 64 in the fastener lateral direction 48 can be not more than a maximum of about 2.54 cm to provide improved performance.

The number and configuration of fastener islands 64 on the fasteners 60 of the invention can vary. A moderate number of fastener islands 64 on a fastener 60 can range from to 2 to about 16; a large number of fastener islands 64 on a fastener 60 would be a number greater than about 16. In addition to the number of fastener islands 64, the total hook area accumulated by the fastener islands 64 will affect the cost, flexibility, grip, skin friendliness and ease of manufacture of the fasteners 60. A low hook area is an area of about 2 cm$^2$ or less; a high hook area is an area of about 8 cm$^2$ or more; a moderate hook area is an area between about 2 cm$^2$ and about 8 cm$^2$. Having a relatively low number of islands 64 combined with a low hook area provides a fastener 60 having low manufacturing cost, high flexibility, low grip and skin friendliness. Increasing the hook area to a moderate hook area increases the cost and improves the grip of the fastener 60; using a high hook area with a low number of islands 64 would have a further increased cost. Having a relatively large number of islands 64 combined with a low hook area provides a fastener 60 having low manufacturing cost, high flexibility, low grip and skin friendliness but also being relatively more difficult to manufacture at high speeds. Increasing the hook area to a moderate hook area increases the cost and improves the grip of the fastener 60; using a high hook area with a large number of islands 64 would have an even higher cost and could have decreased skin friendliness. Based on a balancing of the relevant factors, it is desirable for a fastener 60 to have a relatively low number of fastener islands 64 and a moderate total hook area (the area of hooks not including the "sea" areas between the fastener islands 64). Such fasteners 60 provide the benefits of moderate cost, high flexibility, strong grip and skin friendliness.

Figure 11:
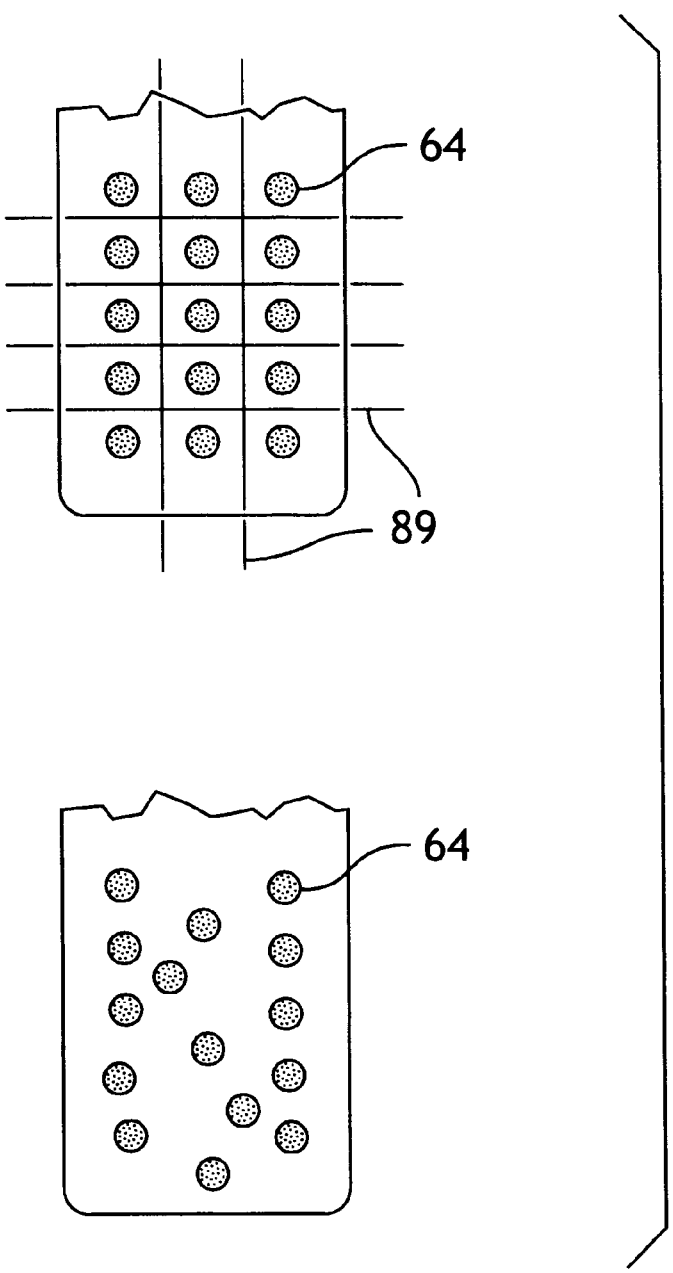
FIG. 11 representatively illustrates a top plan view of two alternate configurations of mechanical fasteners of the present invention having different arrangements of fastener islands to provide different lines of flexure.

The spacing between fastener islands 64 can range from about 3 mm to about 30 mm. The fastener islands 64 can be arranged in any suitable geometry including a "checkerboard" pattern, a chevron pattern and around the perimeter of an oval or other shape. For some fasteners 60, it may be desirable to arrange the fastener islands 64 to create well-defined lines of flexibility by leaving "lines" free of fastener islands 64. For other fasteners 60, it may be desirable to arrange the fastener islands 64 to block lines of flexibility. FIG. 11 depicts two embodiments of fasteners of the present invention: one embodiment shows the fastener islands 64 arranged to create well-defined lines of flexibility 89 while the other embodiment shows the fastener islands 64 arranged so as to block lines of flexibility 89.

Desirably, the mechanical fastening material 66 of the discrete fastener islands 64 of this embodiment of the present invention are a hook fastener material, as already described in detail herein. In particular, the fastening material 66 may be VELCRO HTH 858 or VELCRO HTH 823, or a similar hook material.

The various components of the fastener 60 are integrally assembled together employing various types of suitable attachment means known in the art, such as adhesive, sonic and thermal bonds or combinations thereof. It is generally desirable to have the majority of the components of the fastener 60 be assembled together using ultrasonic bonding techniques for reduced manufacturing cost. For example, as discussed in more detail herein, the planar perimeter edge 70 of the fastener island 64 may be embedded within the flexible layer 62 of the fastener 60 by various attachment means, including sonic bonding.

As representatively illustrated in FIGS. 1–6 and 9, the flexible cloth-like mechanical fastener 60 of the present invention may further define a manufacturer's bond end 84 and a user's end 82. As used herein, reference to a manufacturer's bond end 84 is intended to refer to that portion of a fastener which is attached to the diaper 20 by the manufacturer of the diaper as part of the diaper production process. That is, the manufacturer's bond end 84 is generally intended to be permanently attached to the diaper 20. Likewise, as used herein, reference to a user's end 82 is intended to refer to that portion of the fastener 60 that is used by the wearer or caregiver to secure the diaper 20 about the waist of the wearer, and which generally includes the discrete fastener islands 64. The user's end 82 of the mechanical fastener 60 is generally designed to be refastenable such that the diaper can be fastened and refastened about a wearer through the use of the users end 82 of the mechanical fastener 60. Thus, the attachment formed by the users end 82 of the mechanical fastener 60 is generally nonpermanent.

Methods of bonding the fastener 60 to the diaper 20 to define the bond end 84 are well known to those skilled in the art. For example, as representatively illustrated in FIG. 8, the mechanical fasteners 60 may be permanently adhered to the side edges 30 of the diaper 20 by adhesive bonds, sonic bonds, thermal bonds, and the like, or combinations thereof. As discussed above, the method of attachment used to form the bond end 84 is generally intended to be permanent. Desirably, the bond end 84 is attached to the diaper 20 using ultrasonic bonding techniques for reduced manufacturing cost.

Figure 8:
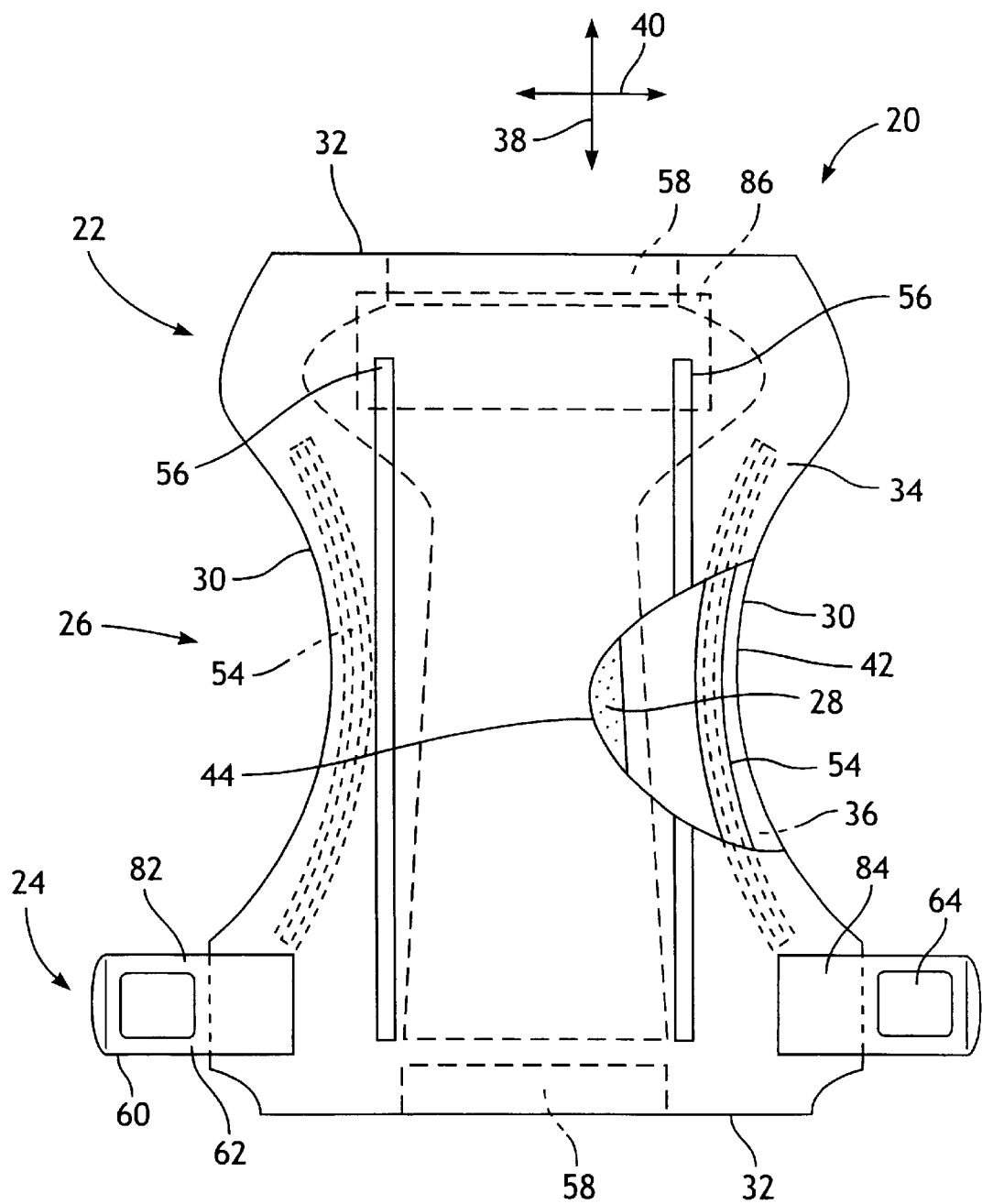
FIG. 8 representatively illustrates a plan view of a disposable absorbent article including mechanical fasteners of the present invention, where the absorbent article is shown in a stretched and laid flat condition with the surface of the article which contacts the wearer's skin facing the viewer and with portions of the article partially cut away to show the underlying features.

FIG. 8 representatively illustrates the mechanical fastener 60 of the present invention included in combination with a disposable diaper 20. In particular, the diaper 20 is shown in an unfastened, stretched and laid flat configuration with the surface of the diaper adapted to contact the wearer's skin facing the viewer and with portions of the diaper partially cut away to show the underlying features. The illustrated diaper 20 defines an absorbent core 28, a front waist region 22, a back waist region 24, a crotch region 26 which extends between and connects the front and back waist regions 22 and 24, a longitudinal direction 38 and a lateral direction 40. As used herein, the term "longitudinal direction" means the direction that is parallel to the machine direction of the diaper 20 and generally corresponds to the "y" direction of the diaper 20. As used herein the term "lateral direction" means the direction that is perpendicular to the machine direction of the diaper 20 and generally corresponds to the "x" direction of the diaper 20. The front waist region 22 includes the portion of the diaper 20 which, when worn, is positioned on the front of the wearer while the back waist region 24 comprises the portion of the diaper 20 which, when worn, is positioned on the back of the wearer. The crotch region 26 of the diaper 20 includes the portion of the diaper 20 which, when worn, is positioned between the legs of the wearer and covers the lower torso of the wearer.

The diaper 20 defines a pair of laterally opposed side edges 30, a pair of longitudinally opposed waist edges 32, an interior surface 34 which is configured to contact the wearer, and an exterior surface 36 opposite the interior surface 34 which is configured to contact the wearer's clothing in use. The illustrated diaper 20 also includes an outer cover 42 and a bodyside liner 44 which is connected to the outer cover 42 in a superposed relation. An absorbent core 28 is located between the outer cover 42 and the bodyside liner 44. The laterally opposed side edges 30 of the diaper 20 are generally defined by the side edges of the outer cover 42 which further define leg openings which may be curvilinear. The waist edges 32 of the diaper 20 are generally defined by the waist edges of the outer cover 42 and define a waist opening which is configured to encircle the waist of the wearer when worn. The absorbent core 28 is configured to contain and/or absorb any body exudates discharged from the wearer. The diaper 20 may further include leg elastics 54, containment flaps 56 and waist elastics 58 as are known to those skilled in the art. It should be recognized that individual components of the diaper 20 may be optional depending upon the intended use of the diaper 20.

Desirably, the fasteners 60 of the present invention may be refastenably engaged directly with the exterior surface 36 of the diaper 20 to refastenably apply the diaper about the lower torso of the wearer. Alternatively, the diaper 20 may further include an attachment panel 86. The attachment panel 86 may be located on the front or back waist region 22 and 24 respectively, opposite the waist region 22 or 24 to which the fasteners 60 are attached. As such, the attachment panel 86 may provide an alternative surface to which the mechanical fasteners 60 may be releasably engaged to form the refastenable diaper 20. For example, in FIG. 8, the attachment panel 86 is shown in phantom lines on the exterior surface 36 of the diaper 20 in the front waist region 22. In another aspect of the present invention, the mechanical fastener 60 is located within the attachment panel 86. The material into which the mechanical fastener 60 engages, such as a loop material, is then located on a lateral extension of the outer cover, such as the location where the fasteners are conventionally attached.

As previously described herein, particular embodiments of the fastener 60 of the present invention, when used in combination with the diaper 20, may improve the fit and comfort of the diaper 20. For example, the improved flexibility of the fasteners of the present invention may reduce the opportunity for the creation of harsh edges in the fastener 60, which may develop in a traditional mechanical fastener in use. As such, the possibility of the fastener red-marking or irritating the wearer's skin is decreased. Moreover, the increased flexibility of the mechanical fastener 60 allows the mechanical fastener 60 to be adjusted to a wider range of positions in use to achieve the optimum fastening location on the diaper 20 for improved fit and comfort.

Desirably, the mechanical fasteners 60 of the present invention are permanently attached to the back waist region 24 of the diaper 20, and refastenably engage the diaper 20 in the front waist region 22 increasing the ease with which the wearer or the caregiver can adjust the fit of the diaper 20. Alternatively, the fasteners 60 may be permanently attached to the front waist region 22 of the diaper 20, and refastenably engage the diaper in the back waist region 24. Such a configuration may be desirable for making the fasteners 60 more difficult for the wearer to access, thereby reducing the opportunity for the wearer to open and remove the diaper 20.

The diaper 20 may be of various suitable shapes. For example, in the unfastened configuration as illustrated in FIG. 8, the diaper may have an overall rectangular shape, T-shape or a generally I-shape. In the shown embodiment, the diaper 20 has an approximately hourglass shape in an unfastened configuration. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference. The various aspects and configurations of the invention can provide distinctive combinations of softness, body conformity, reduced red-marking of the wearer's skin, reduced skin hydration, improved containment of body exudates and improved aesthetics.

The various components of the diaper 20 are integrally assembled together employing various types of suitable attachment means, such as adhesive, sonic and thermal bonds or combinations thereof. In the shown embodiment, for example, the outer cover 42 and bodyside liner 44 are assembled to each other and to the absorbent core 28 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Alternatively, the absorbent core 28 may be connected to the outer cover 42 using conventional fasteners such as buttons, hook and loop type fasteners, adhesive tape fasteners, and the like. The other components of the diaper 20 may be suitably connected together using similar means. Similarly, other diaper components, such as the elastic members 54 and 58 and the fasteners 60, may be assembled into the diaper 20 article by employing the above-identified attachment mechanisms. Desirably, the majority of the diaper components are assembled together using ultrasonic bonding techniques for reduced manufacturing cost.

The outer cover 42 of the diaper 20, as representatively illustrated in FIG. 8, may suitably be composed of a material which is either liquid permeable or liquid impermeable. It is generally preferred that the outer cover 42 be formed from a material which is substantially impermeable to liquids. A typical outer cover can be manufactured from a thin plastic film or other flexible liquid-impermeable material. For example, the outer cover 42 may be formed from a polyethylene film having a thickness of from about 0.013 millimeter (0.5 mil) to about 0.051 millimeter (2.0 mils). If it is desired to present the outer cover 42 with a more cloth-like feeling, the outer cover 42 may comprise a polyolefin film having a nonwoven web laminated to the exterior surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers. The polypropylene fibers have a thickness of about 1.5 to 2.5 denier per filament, which nonwoven web has a basis weight of about 17 grams per square meter (0.5 ounce per square yard). The outer cover 42 may otherwise include bicomponent fibers such as polyethylene/polypropylene bicomponent fibers. Methods of forming such cloth-like outer covers are known to those skilled in the art.

Further, the outer cover 42 may be formed of a woven or nonwoven fibrous web layer which has been totally or partially constructed or treated to impart a desired level of liquid impermeability to selected regions that are adjacent or proximate the absorbent core 28. Still further, the outer cover 42 may optionally be composed of a micro-porous "breathable" material which permits vapors to escape from the absorbent core 28 while still preventing liquid exudates from passing through the outer cover 42. For example, the outer cover 42 may include a vapor permeable non-woven facing layer laminated to a micro-porous film. Suitable "breathable" outer cover materials are described in U.S. Pat. No. 5,695,868 issued to McCormack et al. and U.S. Pat. No. 5,843,056 issued Dec. 1, 1998 to Good et al., the descriptions of which are hereby incorporated by reference. Still further, the outer cover 42 may also be an elastomeric material such as a stretch-thermal laminate (STL), neck-bonded laminate (NBL), or stretch-bonded laminate (SBL) material. Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated by reference. The outer cover 42 can also be embossed or otherwise provided with a matte finish to provide a more aesthetically pleasing appearance.

The bodyside liner 44, as representatively illustrated in FIG. 8, suitably presents a bodyfacing surface which is compliant, soft feeling, and nonirritating to the wearer's skin. Further, the bodyside liner 44 may be less hydrophilic than the absorbent core 28, to present a relatively dry surface to the wearer, and may be sufficiently porous to be liquid permeable, permitting liquid to readily penetrate through its thickness. A suitable bodyside liner 44 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 44 is suitably employed to help isolate the wearer's skin from liquids held in the absorbent core 28.

Various woven and nonwoven fabrics can be used for the bodyside liner 44. For example, the bodyside liner may be composed of a meltblown or spunbonded web of polyolefin fibers. The bodyside liner 44 may also be a bonded-carded web composed of natural and/or synthetic fibers. The bodyside liner 44 may be composed of a substantially hydrophobic material, and the hydrophobic material may optionally be treated with a surfactant or otherwise processed to impart a desired level of wettability and hydrophilicity. In a particular embodiment of the present invention, the bodyside liner 44 comprises a nonwoven, spunbond, polypropylene fabric composed of about 2.8–3.2 denier fibers formed into a web having a basis weight of about 20 grams per square meter and a density of about 0.13 grams per cubic centimeter. The fabric may be surface treated with about 0.3 weight percent of a surfactant commercially available from Hodgson Textile Chemicals, Inc. under the trade designation AHCOVEL Base N-62. The surfactant may be applied by any conventional means, such as spraying, printing, brush coating or the like. The surfactant may be applied to the entire bodyside liner 44 or may be selectively applied to particular sections of the bodyside liner 44, such as the medial section along the longitudinal centerline of the diaper, to provide greater wettability of such sections. The bodyside liner 44 may further include a composition applied thereto that is configured to be transferred to the wearer's skin for improving the skin health of the wearer. Suitable compositions for use on the bodyside liner 44 are described in U.S. Pat. No. 6,149,934 issued Nov. 21, 2000 to Krzysik et al., the disclosure of which is hereby incorporated by reference.

The absorbent core 28 of the diaper 20, as representatively illustrated in FIG. 8, may suitably include a matrix of hydrophilic fibers, such as a web of cellulosic fluff, mixed with particles of a high-absorbency material commonly known as superabsorbent material. In a particular aspect, the absorbent core 28 includes a matrix of cellulosic fluff such as wood pulp fluff and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the absorbent core 28 to better contain and absorb body exudates. The concentration of the superabsorbent particles may also vary through the thickness of the absorbent core 28. Alternatively, the absorbent core 28 may include a laminate of fibrous webs and superabsorbent material or other suitable means of maintaining a superabsorbent material in a localized area.

The absorbent core 28 may have any of a number of shapes. For example, the absorbent core may be rectangular, I-shaped, or T-shaped. It is generally preferred that the absorbent core 28 be narrow in the crotch region 26 of the diaper 20. It has been found that the absorbent core 28 of the present invention is particularly useful when the width dimension in the crotch region 26 is from about 2.5 to about 12.7 centimeters (1.0 to about 5.0 inches), desirably no more than about 7.6 centimeters (3.0 inches) and more desirably no more than about 5.1 centimeters (2.0 inches). The narrow crotch width dimension of the absorbent core 28 allows the absorbent core 28 to better fit between the legs of the wearer. The size and the absorbent capacity of the absorbent core 28 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core 28 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va., DOW DRYTECH 2035LD polymer available from Dow Chemical Co. located in Midland, Mich. and Stockhausen W65431 polymer available from Stockhausen Inc., located in Greensboro, N.C.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent core 28 in an amount of from about 5 to about 90 weight percent based on total weight of the absorbent core 28.

Optionally, a substantially hydrophilic tissue wrapsheet (not illustrated) may be employed to help maintain the integrity of the airlaid fibrous structure of the absorbent core 28. The tissue wrapsheet is typically placed about the absorbent core 28 over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent core 28. The wrapsheet material on one side of the absorbent fibrous mass may be bonded to the wrapsheet located on the opposite side of the fibrous mass to effectively entrap the absorbent core 28.

As representatively illustrated in FIG. 8, the disposable diaper 20 may include a pair of containment flaps 56 that are configured to provide a barrier to the lateral flow of body exudates. The containment flaps 56 may be located along the laterally opposed side edges 30 of the diaper adjacent the side edges of the absorbent core 28. Each containment flap 56 typically defines an unattached edge which is configured to maintain an upright, perpendicular configuration in at least the crotch region 26 of the diaper 20 to form a seal against the wearer's body. The containment flaps 56 may extend longitudinally along the entire length of the absorbent core 28 or may only extend partially along the length of the absorbent core 28. When the containment flaps 56 are shorter in length than the absorbent core 28, the containment flaps 56 can be selectively positioned anywhere along the side edges 30 of diaper 20 in the crotch region 26. In a particular aspect of the invention, the containment flaps 56 extend along the entire length of the absorbent core 28 to better contain the body exudates.

Such containment flaps 56 are generally well known to those skilled in the art. For example, suitable constructions and arrangements for containment flaps 56 are described in U.S. Pat. No. 4,704,116 issued Nov. 3, 1987, to K. Enloe, the disclosure of which is hereby incorporated by reference.

The diaper 20 may further include elastics at the waist edges 32 and side edges 30 of the diaper 20 to further prevent leakage of body exudates and support the absorbent core 28. For example, as representatively illustrated in FIG. 8, the diaper 20 of the present invention may include a pair of leg elastic members 54 which are connected to the laterally opposed side edges 30 of the diaper 20 in the crotch region 26. The diaper 20 may also include a pair of waist elastic members 58 which are connected to the longitudinally opposed waist edges 32 of the diaper 20. The leg elastics 54 and waist elastics 58 are generally adapted to fit about the legs and waist of a wearer in use to maintain a positive, contacting relationship with the wearer to effectively reduce or eliminate the leakage of body exudates from the diaper 20.

Materials suitable for use as the leg elastics 54 and waist elastics 58 are well known to those skilled in the art. Exemplary of such materials are sheets or strands or ribbons of a polymeric, elastomeric material which are adhered to the outer cover 42 in a stretched position, or which are attached to the outer cover 42 while the outer cover is pleated, such that elastic constrictive forces are imparted to the outer cover 42. The leg elastics 54 may also include such materials as polyurethane, synthetic and natural rubber.

The different aspects of the present invention advantageously provide flexible, cloth-like fasteners 60. The mechanical fastener 60 is provided on a thin flexible layer 62 with the mechanical fastening material 66 embedded therein. This configuration provides a mechanical fastener 60 which may be bent or conformed and yet provides reliable securement of the article about the wearer. Moreover, the perimeter edge 70 of the mechanical fastening material 66 is surrounded by the flexible layer 62 while being recessed within the flexible layer 62 thereby reducing the possibility of irritation or red-marking. Further, in certain configurations, the mechanical fastener 60 of the present invention may be provided with multiple discrete islands 64 of fastener material 66. As such, the flexibility of the mechanical fastener 60 is additionally supplemented by providing areas of flexible material between the islands of fastener material 66. This specially located flexible material may be bent instead of the more rigid fastener material. Accordingly, the possibility of creasing the fastener material 66 is also reduced, thereby further reducing the possibility of irritation caused by any rigid edges of the fastener material 66 coming into contact with the wearer's skin.

The mechanical fastener 60 of the present invention may be provided in combination with a disposable absorbent article. As a result, the absorbent article advantageously provides a fastener 60 that enhances the comfort of the wearer by reducing the opportunity for red-marking and irritation. In addition, the increased flexibility of the fasteners 60 of the present invention allows the fasteners 60 to better accommodate the movement of particularly the active wearer, thereby providing more reliable securement of the article about a wearer. The fit and comfort of the article are also similarly enhanced as the flexible fastener may be adjusted to a wider range of positions in use, to achieve the optimum fastening location upon the wearer.

In another aspect, the present invention includes methods by which the fasteners 60 of the present invention can be made. For example, as representatively illustrated in FIG. 10, the methods can include providing a continuous web of nonwoven material 90. The continuous web of nonwoven material 90 may be provided by means known to those skilled in the art. For example, as representatively illustrated in FIG. 10, a continuous web of nonwoven material may be provided by unwinding a roll of the nonwoven material 92. The unwind may be advantageously configured to continually unwind a web of material without interruption (not shown). Desirably, the nonwoven material is a flexible nonwoven material as are well known to those skilled in the art. For example, the nonwoven material may be a neck bonded laminate (NBL) material or a bonded carded web (TBCW).

Figure 10:
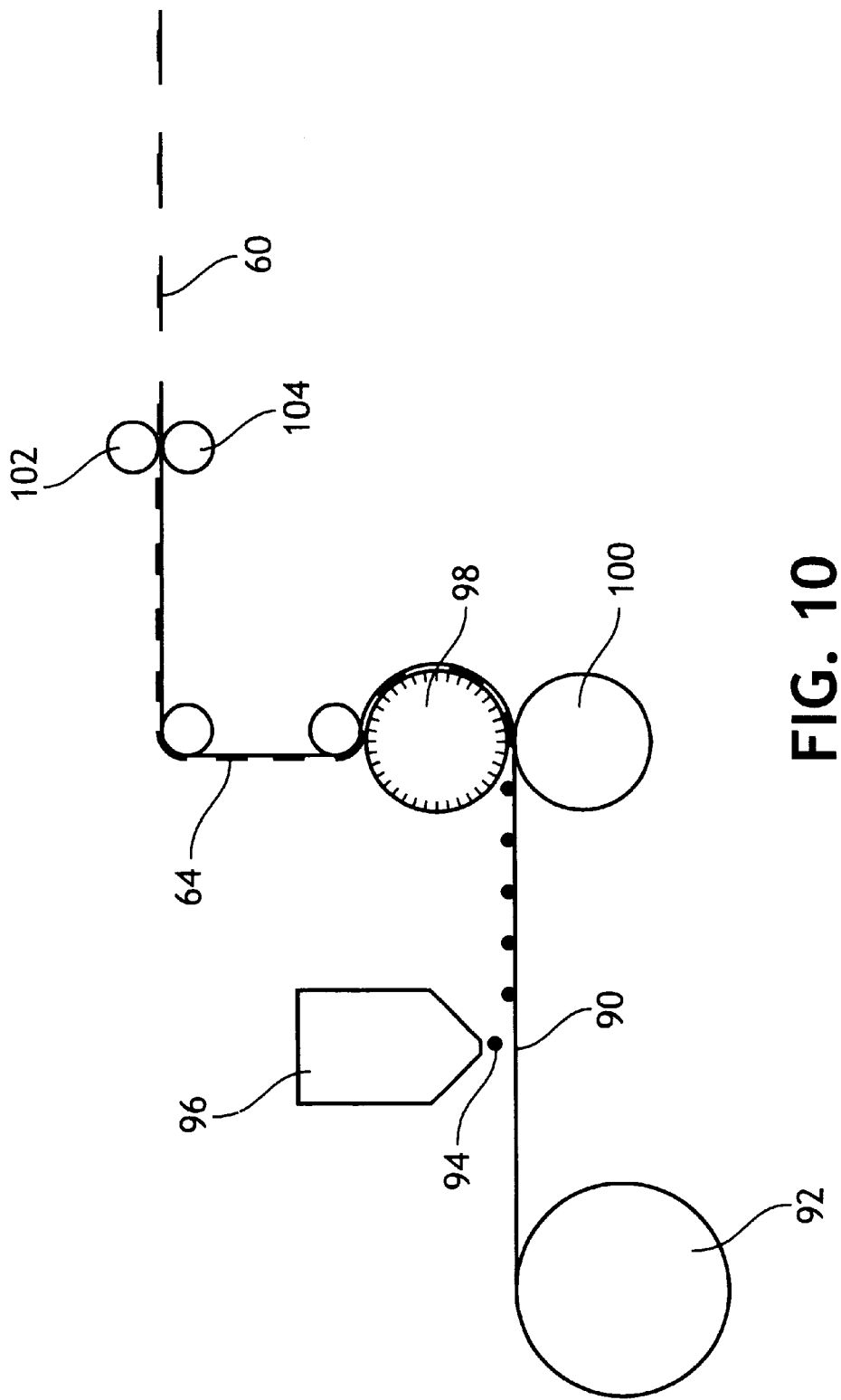
FIG. 10 representatively illustrates a schematic view of an example of a method of making mechanical fasteners of the present invention.

The mechanical fastener 60 of the present invention also includes at least one fastener island 64. As representatively illustrated in FIG. 10, the fastener island 64 may be provided by intermittently applying drops of molten polymer 94 to the nonwoven web 90. The drops of molten polymer 94 may be applied to the nonwoven web 90 in a number of suitable ways as are well know to those skilled in the art. For example, as shown in FIG. 10, the polymer 94 may be applied in molten form onto the nonwoven web 90 using an extruder 96. Desirably, the polymer should be suitably viscous when molten for optimum applicability. Polymers possessing such molten viscosity are well known to those skilled in the art. For example, a suitable polymer may be polypropylene. Other suitable polymers include polyethylene and polyolefins, poly(lactic acid) and polyesters, nylons and polyurethanes. It should be noted that when applying the molten polymer 94 as described above, the nonwoven web 90 should possess melting characteristics such that it does not melt when the drops of molten polymer 94 are applied.

The drops of molten polymer 94 are then molded into the discrete fastener islands 64. Suitable molding methods are well known to those skilled in the art. For example, the continuous nonwoven web 90 carrying drops of molten polymer 94 may be fed into a molding apparatus such as a rotary die or a press. In particular, as representatively illustrated in FIG. 10, a combination of a pressure roller 100 and a rotary die 98 may be used. In the rotary die 98, some of the molten polymer 94 impregnates a discrete section of the nonwoven web forming a backing material 68. As such, the backing material 68 is embedded within the nonwoven web, ensuring that the planar perimeter edge 70 of the fastener islands 64 is surrounded by the nonwoven web.

Simultaneously, another portion of the drop of molten polymer 94 is molded into mechanical fastening material 66. The molten polymer may be molded into a variety of different types of mechanical fastening materials. Desirably, the mechanical fastening material 66 may be molded into a plurality of hooks. The molten polymer may then be chilled and removed from the die, providing a nonwoven web with discrete fastener islands 64. Desirably, the rotary die 98 may be capable of both molding and cooling the molten polymer 94 so that the fastener islands 64 may be formed. For example, this may be accomplished by providing a rotary die 98 that is internally cooled.

The nonwoven web 90 including fastener islands 64 may then be cut into individual mechanical fasteners 60 by being passed through a cutter. Such cutters are generally known to those skilled in the art. For example, as representatively illustrated in FIG. 10, the combination of a cutting roll 102 and an anvil roll 104 may be used, through which the web of mechanical fasteners 60 travels. The anvil roll 104 may include a hardened steel rotating roll while the cutting roll 102 may include one or more flexible hardened steel blades clamped on to another rotating roll. The pinching force between the blade on the cutting roll 102 and the anvil roll 104 creates the cut. The cutting roll 102 may have one or more blades depending upon the desired distance between the cuts. Alternatively, the cutting roll 102 may include a die in the shape of the pattern desired for the mechanical fastener 60 (not shown). For example the pattern may be shaped to provide a nested fastener pattern to advantageously reduce waste. That is, the fasteners 60 may be cut and shaped such that each fastener 60 fits within the negative space created by the adjacent fastener 60 when it is cut from the nonwoven web 90. In the course of cutting the web of mechanical fasteners 60, the nonwoven web 90 imparts to the fasteners 60 a flexible layer 62, which provides the chassis of the mechanical fastener 60.

Alternatively, the mechanical fasteners 60 may remain connected together as a continuous web and be subsequently wound for later use or processing (not shown). As such, the wound roll of mechanical fasteners 60 may advantageously be produced in one location and then unwound and processed in another location for use on, for example, disposable absorbent articles such as diapers.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

We claim:

1. A mechanical fastener defining a fastener longitudinal direction, a fastener lateral direction, and a third direction, said fastener further comprising:
   a) a flexible layer; and
   b) at least one discrete fastener island having a planar perimeter edge, a mechanical fastening material, and a backing material attached to said mechanical fastening material, wherein said backing material is embedded within said flexible layer and said planar perimeter edge is surrounded by said flexible layer.

2. The mechanical fastener according to claim 1 wherein said flexible layer is a nonwoven material.

3. The mechanical fastener according to claim 1 wherein said flexible layer is a thermally bonded carded web.

4. The mechanical fastener according to claim 1 wherein said flexible layer is a neck bonded laminate.

5. The mechanical fastener according to claim 1 wherein said flexible layer is extensible.

6. The mechanical fastener according to claim 1 wherein said flexible layer is a foam material.

7. The mechanical fastener according to claim 1 wherein said flexible layer defines a fastener thickness in said third direction of from about 250 µm to about 2500 µm.

8. The mechanical fastener according to claim 1 wherein said mechanical fastening material is a hook material.

9. The mechanical fastener according to claim 8 wherein said hook material contains multiple hooks.

10. The mechanical fastener according to claim 9 wherein said hook material contains at least 20 hooks.

11. The mechanical fastener according to claim 8 wherein said hook material is a flat top hook material.

12. The mechanical fastener according to claim 1 wherein said backing material is embedded in said flexible layer by ultrasonic bonds.

13. The mechanical fastener according to claim 1 and further comprising a plurality of discrete fastener islands.

14. The mechanical fastener according to claim 1 wherein said flexible layer includes:
 a) a first flexible layer defining an interior surface and an exterior surface opposite said interior surface wherein said backing material of said discrete fastener island is attached to said interior surface of said first flexible layer; and
 b) a second flexible layer attached to said interior surface of said first flexible layer wherein said second flexible layer defines an opening which corresponds to said discrete fastener island and exposes said mechanical fastening material of said discrete fastener island.

15. The mechanical fastener according to claim 1 wherein said fastener further defines a users end and a bond end wherein said bond end is permanently attached to a disposable absorbent article and said users end contains said discrete fastener island and is configured to secure said disposable absorbent article about a wearer.

16. A mechanical fastener defining a fastener longitudinal direction, a fastener lateral direction, and a third direction, said fastener further comprising:
 a) a nonwoven layer; and
 b) a plurality of discrete fastener islands having a planar perimeter edge, a mechanical fastening material, and a backing material attached to said mechanical fastening material, wherein said backing material of each of said discrete fastener islands is embedded within said nonwoven layer and said planar perimeter edge of each of said discrete fastener islands is surrounded by said nonwoven layer.

17. The mechanical fastener according to claim 16 wherein said planar perimeter edge of said discrete fastener islands has a generally circular shape.

18. The mechanical fastener according to claim 16 wherein said nonwoven layer is a thermally bonded carded web.

19. The mechanical fastener according to claim 16 wherein said nonwoven layer is a neck bonded laminate.

20. The mechanical fastener according to claim 16 wherein said nonwoven layer is extensible.

21. The mechanical fastener according to claim 16 wherein said nonwoven layer defines a fastener thickness in said third direction of from about 250 µm to about 2500 µm.

22. The mechanical fastener according to claim 16 wherein said mechanical fastening material is a hook material.

23. The mechanical fastener according to claim 22 wherein said hook material contains multiple hooks.

24. The mechanical fastener according to claim 23 wherein said hook material contains at least about 20 hooks.

25. The mechanical fastener according to claim 22 wherein said hook material is a flat top hook material.

26. The mechanical fastener according to claim 16 wherein said backing material is embedded in said nonwoven layer by ultrasonic bonds.

27. The mechanical fastener according to claim 16 wherein said nonwoven layer includes:
 a) a first nonwoven layer defining an interior surface and an exterior surface opposite said interior surface wherein said backing material of said discrete fastener islands is attached to said interior surface of said first nonwoven layer; and
 b) a second nonwoven layer attached to said interior surface of said first nonwoven layer wherein said second nonwoven layer defines a plurality of openings which correspond to said discrete fastener islands and expose said mechanical fastening material of said discrete fastener islands.

28. The mechanical fastener according to claim 16 wherein said fastener further defines a users end and a bond end wherein said bond end is permanently attached to a disposable absorbent article and said users end contains said discrete fastener islands and is configured to secure said disposable absorbent article about a wearer.

29. A disposable absorbent article comprising:
 a) an outer cover;
 b) a bodyside liner;
 c) an absorbent core located between said bodyside liner and said outer cover;
 d) at least one mechanical fastener comprising:
  i) a nonwoven layer; and
  ii) a plurality of discrete fastener islands having a planar perimeter edge, a mechanical fastening material, and a backing material attached to said mechanical fastening material, wherein said backing material of each of said discrete fastener islands is embedded within said nonwoven layer and said planar perimeter edge of each of said discrete fastener islands is surrounded by said nonwoven layer, and wherein said mechanical fastener is configured to refastenably secure said disposable absorbent article about a wearer.

30. The disposable absorbent article according to claim 29 wherein said mechanical fastening material is a hook material.

31. The disposable absorbent article according to claim 29 wherein said mechanical fastener is configured to refastenably engage directly to said outer cover.

32. The disposable absorbent article according to claim 29 and further comprising an attachment panel wherein said mechanical fastener is configured to refastenably engage said attachment panel.

33. The disposable absorbent article according to claim 29 wherein said nonwoven layer is a neck bonded laminate.

34. The disposable absorbent article according to claim 29 wherein said nonwoven layer is a thermally bonded carded web.

35. A mechanical fastener made by a process which comprises the steps of:
 a) providing a continuous nonwoven web;
 b) intermittently applying drops of a molten polymer to said nonwoven web;
 c) molding said drops of molten polymer into a plurality of discrete fastener islands to provide a backing material and a mechanical fastening material in each of said discrete fastener islands; and d) chilling said discrete fastener islands, and embedding said backing material within said nonwoven web to provide a continuous web of mechanical fasteners.

36. The mechanical fastener according to claim 35 wherein said mechanical fastening material is a hook fastening material.

37. The mechanical fastener according to claim 35 wherein said nonwoven web is a neck bonded laminate.

38. The mechanical fastener according to claim 35 wherein said nonwoven web is a thermally bonded carded web.

39. The mechanical fastener according to claim 35 wherein the process further includes the step of cutting individual fasteners from said continuous web of mechanical fasteners.

40. The mechanical fastener of claim 39 wherein said fastener defines a shape which is configured to be nested within an adjacent individual fastener from said continuous web of mechanical fasteners.

41. The mechanical fastener according to claim 35 wherein the process further includes the step of winding said continuous web of mechanical fasteners for later use.

42. A disposable absorbent article comprising:

a) an outer cover;

b) a bodyside liner;

c) an absorbent core located between said bodyside liner and said outer cover;

d) at least one mechanical fastener located on the outer cover comprising:

i) a nonwoven layer; and ii) a plurality of discrete fastener islands having a planar perimeter edge, a mechanical fastening material, and a backing material attached to said mechanical fastening material, wherein said backing material of each of said discrete fastener islands is embedded within said nonwoven layer and said planar perimeter edge of each of said discrete fastener islands is surrounded by said nonwoven layer, and wherein said mechanical fastener is configured to refastenably secure said disposable absorbent article about a wearer.

* * * * *

UNITED STATES PATENT AND TRADEMARK OFFICE
CERTIFICATE OF CORRECTION

PATENT NO. : 6,730,069 B2
DATED : May 4, 2004
INVENTOR(S) : Richard Warren Tanzer, Karen Marie Menard and Julius Charles Nagy It is certified that error appears in the above-identified patent and that said Letters Patent is hereby corrected as shown below:

Column 3,
Line 45, delete the last "9" of "5,782,8199".

Column 11,
Line 49, delete the last "9" of "5,782,8199".

Signed and Sealed this

Tenth Day of May, 2005

JON W. DUDAS
*Director of the United States Patent and Trademark Office*